United States Patent [19]
Torija et al.

[11] Patent Number: 4,952,592
[45] Date of Patent: Aug. 28, 1990

[54] 1,4-DIHYDRO 2,6-DIMETHYL 4-(2,3-METHYLENEDIOXYPHENYL) 3-ALKOXY CARBONYL 5-[2-(SUBSTITUTED AMINO)ETHOXY]CARBONYL PYRIDINE

[75] Inventors: Carlos F. Torija; Joaquin A. Galiano Ramos, both of Madrid, Spain

[73] Assignee: Instituto de Investigacion Y Desarrollo Quimicobiologico S.A., Madrid, Spain

[21] Appl. No.: 227,373

[22] Filed: Aug. 2, 1988

[30] Foreign Application Priority Data

Aug. 7, 1987 [EP] European Pat. Off. .......... 87401799

[51] Int. Cl.$^5$ ................ C07D 405/02; A61K 31/455
[52] U.S. Cl. .................................... 514/338; 514/333; 546/270; 546/256
[58] Field of Search ................ 546/270, 256; 514/333, 514/338

[56] References Cited

U.S. PATENT DOCUMENTS

| | | | |
|---|---|---|---|
| 3,441,648 | 4/1969 | Bernard et al. | 546/321 |
| 4,031,104 | 6/1977 | Bossert et al. | 546/256 |
| 4,722,931 | 2/1988 | Cassanova | 514/338 |

FOREIGN PATENT DOCUMENTS 0174131 12/1986 European Pat. Off. .
078186 5/1984 Japan .

OTHER PUBLICATIONS

Cassanova et al., CA 105:172299g.

*Primary Examiner*—Jane T. Fan
*Attorney, Agent, or Firm*—Arnold, White & Durkee

[57] ABSTRACT

1,4 dihydropyridines of general formula:

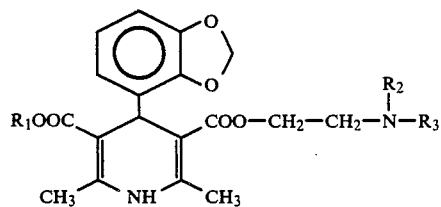

in which:
 $R_1$ is a linear or branched C1–C4 alkyl group;
 $R_2$ is formyl or a C1–C2 alkyl group;
 $R_3$ is a 2-, 3-, 4-picolyl, 2-thienylmethyl, or 4-fluorobenzyl group.

These compositions have properties which are effective in the treatment of hypertension, cardiac ischemia, angina pectoris or other cardiac problems and may be incorporated in pharmaceutically acceptable vehicles.

15 Claims, No Drawings

1,4-DIHYDRO 2,6-DIMETHYL 4-(2,3-METHYLENEDIOXYPHENYL) 3-ALKOXY CARBONYL 5-[2-(SUBSTITUTED AMINO)ETHOXY]CARBONYL PYRIDINE

The present invention relates to new compounds having especially potent calcium-antagonist properties. They are useful in the treatment of angina pectoris, heart attack, hypertension and other cardiovascular problems.

The compounds according to the invention are chemically related to calcium blockers of the 1,4-dihydropyridine group, such as OXODIPINE, and show relaxant effects on cardiac and vascular muscles.

OXODIPINE (formula (I)), synthesized by one of the authors of the present invention, and recommended especially for treating an essential hypertension of slight to moderate intensity, already represented an improvement compared with NIFEDIPINE (formula (II)), in the sense of an improved stability and a longer-lasting effect.

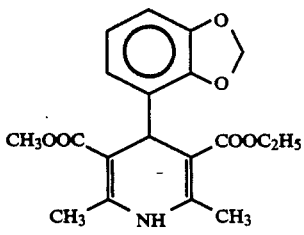

OXODIPINE (I)

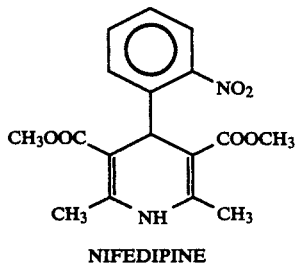

NIFEDIPINE (II)

The compounds of the present invention are new 1,4-dihydropyridines, endowed with a very high vasodilatory activity and hence with antianginal and antihypertensive properties. These new compounds, of general formula (III)

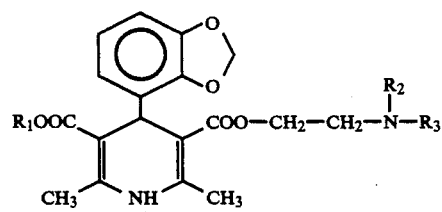

(III)

in which:
$R_1$ denotes a substituted or unsubstituted, linear or branched $C_1$–$C_4$ alkyl group, such as methyl, ethyl, propyl, isopropyl, butyl, isobutyl or methoxyethyl,
$R_2$ denotes a $C_1$–$C_2$ radical such as methyl, formyl or ethyl, and
$R_3$ denotes a hydrogen atom or a substituted or unsubstituted aromatic ring, such as 2-, 3- or 4-picolyl, thienyl or 4-fluorobenzyl,
are characterized, like OXODIPINE, by the presence of a 4-(2,3-methylenedioxyphenyl) radical.

The presence of an asymmetric carbon (C4) indicates the possibility of 2 enantiomers. The presence of an amino group permits the existence of salts such as hydrochloride, sulphate, or the like, using pharmaceutically acceptable organic or inorganic acids.

The present invention also relates to a process for manufacturing these compounds, consisting in treating 2,3-methylenedioxybenzaldehyde (IV):

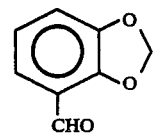

(IV)

with an acetoacetic ester of formula (V) or (VIII):

$$CH_3-COCH_2-COOR_1 \quad (V)$$

$$CH_3-COCH_2-COOCH_2-CH_2-N\genfrac{}{}{0pt}{}{R_2}{R_3} \quad (VIII)$$

where $R_1$, $R_2$ and $R_3$ have the same meaning as in the formula (III), and then in treating the resulting α-acetyl-β-(2,3-methylenedioxyphenyl)acrylic ester, of formula (VI) or (IX):

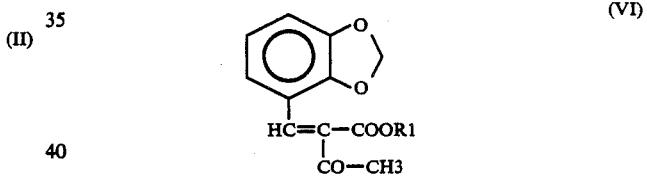

(VI)

(IX)

where $R_1$, $R_2$ and $R_3$ retain the same meanings, with a 3-aminocrotonic ester of formula (VII) or (X):

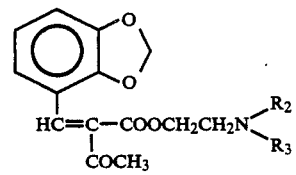

(VII)

(X)

where $R_1$, $R_2$ and $R_3$ have the same meaning as in the formula (III).

The acetoacetic esters are obtained by the treatment of diketene with the appropriate substituted alcohol.

The present invention includes the pharmaceutically acceptable preparations of the compounds of formula (III), which can be administered orally or rectally, nasally, sublingually or parenterally. These preparations consist of a mixture of the active principle, optionally in the form of a pharmaceutically acceptable salt, with a vehicle which can be solid, semi-solid or liquid, or in the form of capsules to be taken by mouth, thereby forming another aspect of the invention.

In general, the active principle constitutes 0.1% to 99% by weight of the preparation, for example 0.5 to 10% for the injectable preparations, and between 10 and 80% for the preparations for oral use.

In the case of a pharmaceutical preparation containing a compound according to the invention, in the form of unit doses for oral application, the active principle may be mixed with a pulverulent solid such as lactose, sucrose, sorbitol, or alternatively wheat starch, amylopectin, agar, or a cellulose derivative, polyvinylpyrrolidone or gelatin, and can also comprise lubricants such as magnesium stearate or polyethylene glycol waxes (Carbowax), and can then be made into the form of tablets or of cores for pills.

If pills are selected, the cores can be coated, for example with a concentrated sugar solution which can contain gum acacia, talc, with or without titanium oxide, or alternatively with a film-forming agent dissolved in a volatile organic solvent. Colourings may be added, for example to distinguish the different doses of active substance.

To prepare soft capsules, the active principle can be dissolved in a suitable oil, such as olive, sesame or groundnut oil. Hard capsules can contain granules of the active principle, made with a pulverulent solid vehicle, such as lactose, sucrose, starch, cellulose derivatives, polyvinylpyrrolidone or gelatin, with or without a lubricant such as magnesium stearate or stearic acid.

Slow-release, or delayed-release, forms may also be prepared, using suitable excipients. Different processes may be employed for controlling the availability: microgranules or coated particles, cores having successive layers or slightly soluble forms.

Lastly, liquid pharmaceutical forms for oral administration may be prepared: elixirs, syrups or suspensions. For example, it is possible to use a solution containing 0.1 to 10% by weight of active principle, with sugar in an alcohol/water/glycerin mixture, or propylene glycol, flavoured or otherwise, containing saccharin, carboxymethylcellulose or pectin as a dispersant agent.

For parenteral administration, aqueous solutions may be prepared, containing 0.1 to 0.5% of the active principles according to the invention, capable of forming salts with acids such as hydrochloric, phosphoric or tartaric acid, or other organic or inorganic acids. Unit doses of the solution, optionally stabilized or buffered, may advantageously be presented in ampoules or bottles.

The dosage can vary and depends on several factors, such as the patient's condition. Preferred doses range from 10 to 50 mg, administered 1 to 3 times daily. Parenterally, the dose administered is generally from 1 to 10 mg.

A few examples of preparation of the compounds of the invention will be given in order to illustrate the latter, the invention not, however, being limited to these examples.

EXAMPLE I

3-Methyl 5-[2-(N-methylamino)ethyl]1,4-dihydro-2,6-dimethyl-4-(2,3-methylenedioxyphenyl)-3,5-pyridinedicarboxylate.

0.5 g (0.97 mmol) of 3-methyl 5-[2-(N-methyl-N-benzylamino)ethyl]1,4-dihydro-2,6-dimethyl-4-(2,3-methylenedioxyphenyl)-3,5-pyridinedicarboxylate hydrochloride (prepared according to Spanish Pat. No. 536,537), 15 ml of dried ethanol and 110 mg of palladinized charcoal (10% palladium) are introduced into a 100-ml autoclave.

The reaction mixture is maintained under a hydrogen pressure of 10 psi for 20 minutes, with stirring.

The mixture is then filtered on Whatman paper to remove the catalyst, and the solvent is evaporated off under vacuum. An oil is obtained, which is ground with diisopropyl ether. After filtration, 0.42 g of a crystalline powder is collected.

In TLC, the hydrochloride gives a single spot (chloroform/acetone, 5:1 by volume).

IR spectrum (KBr)
  3,600–2,600 cm$^{-1}$ (several bands, amine hydrochloride).
  1,700–1,680 cm$^{-1}$ (C=0, ester group).

The hydrochloride obtained is suspended in 5 ml of 2N sodium hydroxide solution, and the mixture is stirred for 10 minutes. After extraction with twice 10 ml of chloroform, the organic layer is separated off after settling has occurred and dried over anhydrous sodium sulphate, and the solvent is evaporated off under vacuum. The residue is crystallized in diisopropyl ether.

0.36 g (83%) of a crystallized white solid is obtained. M.p. 144°–146° C.

IR spectrum (KBr)
  3,310 cm$^{-1}$ (N—H, of the dihydropyridine ring)
  3,200 cm$^{-1}$ (N—H, of the N-methylaminoethyl side chain)
  1,715–1,700 cm$^{-1}$ (C=0, ester groups)
  1,660 cm$^{-1}$ (C=C of the dihydropyridine)

EXAMPLE II

3-Methyl 5-[2-(N-formyl-N-methylamino)ethyl]1,4-dihydro-2,6-dimethyl-4-(2,3-methylenedioxyphenyl)-3,5-pyridinedicarboxylate.

(a) 2-(N-Formyl-N-methylamino)ethanol:

6 ml (98 mmol) of methyl formate are added with stirring in two portions to a round-bottomed flask containing 5.2 ml (66 mmol) of 2-(N-methylamino)ethanol, the temperature of the mixture being maintained below 50° C. since the reaction is exothermic.

After 40 minutes' stirring, the excess methyl formate and the methanol produced during the reaction are removed under vacuum. 5.8 g of product are obtained in the form of a colourless liquid, which is used as it is for the following stage (100% yield).

IR spectrum (KBr)
  3,600–3,100 cm$^{-1}$ (OH with hydrogen bonds) 1,650 cm$^{-1}$ (C=0, formamide)

(b) 2-(N-Formyl-N-methylamino)ethyl acetylacetate:

19.27 g (187 mmol) of 2-(N-formyl-N-methylamino)ethanol and 65 mg (0.8 mmol) of freshly fused sodium acetate are heated to about 75°–85° C. in a round-bottomed flask equipped with a condenser and a dropping funnel. 15.61 g (187 mmol) of ketene dimer are then added dropwise, the temperature being maintained in the range 75°–85° C. When the addition is complete, the mixture is stirred for a further hour at 75°–85° C.

34.41 g (100%) of a brownish oil are obtained, and this is used without distillation for the following stage.
IR spectrum (KBr)
  1,740 and 1,710 cm$^{-1}$ (C=O, ester and ketone groups)
  1,660 cm$^{-1}$ (C=O, formamide)

(c) 2-(N-Formyl-N-methylamino)ethyl α-acetyl-β-(2,3-methylenedioxyphenyl)acrylate 2.5 g (16.6 mmol) of 2,3-methylenedioxybenzaldehyde and 3.2 g of 2-(N-formyl-N-methylamino)ethyl acetylacetate are dissolved in 7 ml of dry benzene in a round-bottomed flask connected to a Dean & Stark separator containing dry benzene. The mixture is heated until dissolution has taken place, and 0.06 ml of piperidine and 0.2 ml of glacial acetic acid are then added. The resulting solution is brought to reflux for 1 hour until no more water is removed. After being cooled, the mixture is diluted with 30 ml of benzene and washed with twice 30 ml of 5% strength hydrochloric acid and then twice 30 ml of 5% strength sodium bicarbonate and finally with 30 ml of water. The organic layer is separated off after settling has occurred, dried over anhydrous magnesium sulphate and evaporated under vacuum. The resulting oil is washed with 15 ml of ether to remove the unreacted benzaldehyde. After evaporation of the residual solvent, 2.7 g (51%) of viscous brown oil are obtained. This is used as it is for the following stage.
IR spectrum (KBr)
  1,720 cm$^{-1}$ (C=O, ester)
  1,680–1,640 cm$^{-1}$ (C=C and C=O of the ketone and formamide groups)

(d) 3-Methyl 5-[2-(N-formyl-N-methylamino)ethyl]1,4-dihydro-2,6-dimethyl-4-(2,3-methylenedioxyphenyl)-3,5-pyridinedicarboxylate:

2.7 g (8.4 mmol) of 2-(N-formyl-N-methylamino)ethyl α-acetyl-β-(2,3-methylenedioxyphenyl)acrylate and 0.96 g (8.4 mmol) of methyl 3-aminocrotonate are dissolved in 10 ml of isopropanol.

The mixture is maintained for 2 days at 37° C. in an oven, and the solvent is then evaporated under vacuum. The residual oil is treated with an N-hexane/diisopropyl ether mixture, to obtain a clear oil which crystallizes. The solid is collected by filtration and 2.9 g (83%) of yellow-white crystals are obtained.
M.p. 142°–144° C.
IR spectrum (KBr)
  3,260 cm$^{-1}$ (N—H of the pyridine ring)
  1,700–1,690 cm$^{-1}$ (C=O, ester groups)
  1,660–1,640 cm$^{-1}$ (C=O formamide, and C=C of the dihydropyridine)

EXAMPLE III

3-Methyl 5-[2-(N-formyl-N-benzylamino)ethyl]1,4-dihydro-2,6-dimethyl-4-(2,3-methylenedioxyphenyl)-3,5-pyridinedicarboxylate.

(a) 2-(N-formyl-N-benzylamino)ethanol:

10 g (66 mmol) of 2-(N-benzylamino)ethanol are mixed with 7.5 ml (121 mmol) of methyl formate. The mixture is stirred for 3 hours at 50°–60° C., and the excess methyl formate is removed under vacuum with the methanol produced; 11.9 g of colourless liquid are obtained, and this is used without distillation for the following stage (100% yield).
IR spectrum (KBr)
  3,600–3,200 cm$^{-1}$ (OH with hydrogen bonds)
  1,680–1,650 cm$^{-1}$ (C=O, formamide)

(b) 2-(N-Formyl-N-benzylamino)ethyl acetylacetate:

This compound is prepared by the reaction of 2-(N-formyl-N-benzylamino)ethanol and ketene dimer, as described in Example IIb. The product obtained is used as it is for the following stage (100% yield).
IR spectrum (KBr)
  1,760 and 1,730 cm$^{-1}$ (C=O of the ester and ketone groups)
  1,680–1,660 cm$^{-1}$ (C=O, formamide)

(c) 2-(N-Formyl-N-benzylamino)ethyl α-acetyl-β-(2,3-methylenedioxyphenyl)acrylate:

This compound is prepared by the reaction of 2-(N-formyl-N-benzylamino)ethyl acetylacetate and 2,3-methylenedioxybenzaldehyde, according to the process described in Example IIc.

The crude product is treated with an ethyl ether/petroleum ether mixture to remove the residual starting benzaldehyde, and an orange oil is obtained (55% yield).
IR spectrum (KBr)
  1,740 cm$^{-1}$ (C=O, ester)
  1,710–1,670 cm$^{-1}$ (C=C, C=O of the ketone and formamide groups)

(d) 3-Methyl 5-[2-(N-formyl-N-benzylamino)ethyl]1,4-dihydro-2,6-dimethyl-4-(2,3-methylenedioxyphenyl)-3,5-pyridinedicarboxylate This compound is prepared by the reaction of 2-(N-formyl-N-benzylamino)ethyl α-acetyl-β-(2,3-methylenedioxyphenyl)acrylate and methyl 3-aminocrotonate, according to the process described in Example IId.

The product is recrystallized in ethanol, and gives a slightly yellow crystallized solid (76% yield).
M.p. 165°–167° C.
IR spectrum (KBr)
  3,300 cm$^{-1}$ (N—H of the dihydropyridine)
  1,715–1,700 cm$^{-1}$ (C=O of the ester groups)
  1,680–1,650 cm$^{-1}$ (C=O, formamide, and C=C of the dihydropyridine ring).

EXAMPLE IV

3-Methyl 5-{2-[N-methyl-N-(2-picolyl)amino]ethyl}1,4-dihydro-2,6-dimethyl-4-(2,3-methylenedioxyphenyl)-3,5-pyridinedicarboxylate.

(a) 2-[N-Methyl-N-(2-picolyl)amino]ethanol:

57.6 ml (0.72 mol) of 2-(N-methylamino)ethanol, 30 ml of water and 34.02 g (0.405 mol) of sodium bicarbonate are introduced under a nitrogen atmosphere into a round-bottomed flask. The mixture is stirred vigorously and heated to 90°–95° C. 30 g of 2-picolyl chloride (hydrochloride) are added in 3 portions, in the form of 3 freshly prepared solutions of 10 g in 25 ml of water, the addition being spread over 1 hour. After the addition is complete, the mixture is stirred for a further 3 hours at 90°–95° C. The water is then removed under vacuum, and the residual oil is left to cool and then filtered to separate off the precipitated inorganic salts. The filtrate is diluted with 400 ml of chloroform, and the resulting solution is washed with twice 400 ml of 5% strength sodium bicarbonate and then dried over anhydrous potassium carbonate. The solvent is removed under reduced pressure, giving 23.19 g (76%) of a clear oil which is used as it is, without purification, for the following stage.

IR spectrum (KBr)
  3,600–3,200 cm$^{-1}$ (OH with hydrogen bonds)

(b) 2-[N-Methyl-N-(2-picolyl)amino]ethyl acetylacetate:

This compound is prepared by the reaction of 2-[N-methyl-N-(2-picolyl)amino]ethanol and ketene dimer according to the process described in Example IIb; a black liquid is obtained, showing 3 spots in TLC (chloroform/acetone, 5:1, UV lamp at 245 nm).

The crude product is unstable when heated to the boiling point under 8–9 mm of mercury, and it is hence used without purification for the following stage.

IR spectrum (KBr)
  1,740 cm$^{-1}$ (ester)
  1,710 cm$^{-1}$ (C=O, ketone group)

(c) 2-[N-Methyl-N-(-2-picolyl)amino]ethyl 3-aminocrotonate:

5 g of 2-[N-methyl-N-(2-picolyl)amino]ethyl acetylacetate are dissolved in 7 ml of methanol in a round-bottomed flask equipped with a thermometer and a gas inlet. The solution is cooled in an ice/water mixture, and a stream of ammonia is passed through it until the reaction mixture is saturated (approximately 2 hours), the temperature being maintained below 25° C. The solvent is then evaporated off under vacuum, giving a black oil which is purified by boiling in isopropyl ether, followed by separation of the insoluble fraction, to obtain 4.1 g of orange oil.

IR spectrum (KBr)
  3,400 and 3,300 cm$^{-1}$ (NH$_2$)
  1,660 cm$^{-1}$ (C=O, conjugated ester)
  1,620–1,610 cm$^{-1}$ (C=C)

(d) 3-Methyl 5-{2-[N-methyl-N-(2-picolyl)amino]ethyl}1,4-dihydro-2,6-dimethyl-4-(2,3-methylenedioxyphenyl)-3,5-pyridinedicarboxylate dihydrochloride:

2 g (8 mmol) of methyl α-acetyl-β-(2,3-methylenedioxyphenyl)acrylate and 2.05 g (8.7 mmol) of 2-[N-methyl-N-(2-picolyl)amino]ethyl 3-aminocrotonate are dissolved in 15 ml of isopropanol. The solution is left to stand for 2 days at 37° C., and the solvent is removed under vacuum. The residual oil is treated with isopropyl ether in the heated state, and gives an insoluble fraction which is collected by separation after settling has occurred. The remaining ether is removed under vacuum, and the solid is dissolved in 20 ml of isopropanol. After the reaction mixture is cooled in an ice/water mixture, 1.3 ml of hydrochloric acid (6.4N) in isopropanol are added dropwise. The solid which precipitates is left to crystallize for 3 days, and is separated off by filtration. After crystallization in isopropanol, 1.7 g (39%) of dihydrochloride are obtained.

On NMR analysis, a little isopropanol appears, causing solvation of the crystals of the compound. M.p. 161°–164° C., with decomposition.

IR spectrum (KBr)
  3,700–2,500 cm$^{-1}$ (several bands, amine and pyridine in the form of hydrochlorides)
  1,710 and 1,690 cm$^{-1}$ (C=O, ester)

EXAMPLE V

3-Methyl 5{2-[N-methyl-N-(4-picolyl)amino]ethyl}1,4-dihydro-2,6-dimethyl-4-(2,3-methylenedioxyphenyl)-3,5-pyridinedicarboxylate.

(a) 2-[N-Methyl-N-(4-picolyl)amino]ethanol:

This compound is prepared from 4-picolyl chloride and 2-(N-methylamino)ethanol, according to the process described in Example IVa; an oil is obtained, and this is used as it is, without purification, for the following stage (79% yield).

IR spectrum (KBr)
  3,600–3,100 cm$^{-1}$ (OH with hydrogen bonds)

(b) 2-[N-Methyl-N-(4-picolyl)amino]ethyl acetylacetate:

This compound is prepared by the reaction of 2-[N-methyl-N-(4-picolyl)amino]ethanol and ketene dimer, as described in Example IIb. The product is used as it is for the following stage, without purification.

IR spectrum (KBr)
  1,760 cm$^{-1}$ (C=O, ester)
  1,735 cm$^{-1}$ (C=O, ketone group)

(c) 2-[N-Methyl-N-(4-picolyl)amino]ethyl 3-aminocrotonate:

This compound is prepared from the corresponding acetylacetate, according to the process described in Example IVc.

IR spectrum (KBr)
  3,400 and 3,300 cm$^{-1}$ (NH$_2$)
  1,660 cm$^{-1}$ (C=O, conjugated ester)
  1,620–1,610 cm$^{-1}$ (C=C)

(d) 3-Methyl 5{2-[N-methyl-N-(4-picolyl)amino]ethyl}1,4-dihydro-2,6-dimethyl-4-(2,3-methylenedioxyphenyl)-3,5-pyridinedicarboxylate:

This compound is obtained by the reaction of methyl α-acetyl-β-(2,3-methylenedioxyphenyl)acrylate and 2-[N-methyl-N-(4-picolyl)amino]ethyl 3-aminocrotonate, according to the process described in Example IVd. The product cannot be obtained in the crystallized state, since it is hygroscopic. It is obtained in the form of an amorphous, hygroscopic solid by suspension in anhydrous ethyl acetate, followed by evaporation of the solvent under vacuum (41% yield).

IR spectrum (KBr)
  3,600–2,400 cm$^{-1}$ (several bands, amine hydrochloride and pyridine hydrochloride)
  1,700–1,680 cm$^{-1}$ (C=O, ester)

EXAMPLE VI

3-Methyl 5-{2-[N-methyl-N-(3-picolyl)amino]ethyl}1,4-dihydro-2,6-dimethyl-4-(2,3-methylenedioxyphenyl)-3,5-pyridinedicarboxylate.

(a) 2-[N-Methyl-N-(3-picolyl)amino]ethanol:

This compound is prepared from 3-picolyl chloride and 2-(N-methylamino)ethanol, according to the process described in Example IVa; an oil is obtained, and this is used directly for the following stage, without purification (77% yield).

IR spectrum (KBr)
  3,600–3,100 cm$^{-1}$ (OH with hydrogen bond)

(b) 2-[N-Methyl-N-(3-picolyl)amino]ethyl acetylacetate:

This compound is prepared by the reaction of 2-[N-methyl-N-(3-picolyl)amino]ethanol and ketene dimer, as described in Example IIb. The product is used as it is for the following stage, without purification.

IR spectrum (KBr)
  1,760–1,750 cm$^{-1}$ (C=O, ester)
  1,735–1,725 cm$^{-1}$ (C=O, ketone group)

(c) 2-[N-Methyl-N-(3-picolyl)amino]ethyl 3-aminocrotonate:

This compound is prepared from the corresponding acetylacetate, according to the process described in Example IVc.

IR spectrum (KBr)

3,450 and 3,350 cm$^{-1}$ (NH$_2$)
1,680–1,670 cm$^{-1}$ (C=O, conjugated ester)

(d) 3-Methyl 5-{2-[N-methyl-N-(3-picolyl)amino]ethyl}1,4-dihydro-2,6-dimethyl-4-(2,3-methylenedioxyphenyl)-3,5-pyridinedicarboxylate dihydrochloride:

This compound is obtained by the reaction of methyl α-acetyl-β-(2,3-methylenedioxyphenyl)acrylate and 2-[N-methyl-N-(3-picolyl)amino]ethyl 3-aminocrotonate, according to the process described in Example IVd. As a result of its hygroscopic nature, the product cannot be obtained in crystalline form. It may be obtained in the form of a hygroscopic, amorphous solid, by boiling in diisopropyl ether and filtration. It is then dissolved in water and the solution washed with chloroform and alkalinized to pH 10 with 5N sodium hydroxide. After extraction with chloroform, the organic layer is dried over anhydrous magnesium sulphate, and the solvent is evaporated off under vacuum. An oil is obtained which crystallizes in diisopropyl ether. The base is a yellow-white crystalline powder, m.p. 139°–141° C. (43% yield).

IR spectrum (KBr) of the base:
1,710 and 1,700 cm$^{-1}$ (C=O, ester)
1,655 and 1,635 cm$^{-1}$ (C=C)

EXAMPLE VII

3-Methyl 5-{2-[N-methyl-N-(4-fluorobenzyl)amino]ethyl}1,4-dihydro-2,6-dimethyl-4-(2,3-methylenedioxyphenyl)-3,5-pyridinedicarboxylate.

(a) 2-[N-Methyl-N-(4-fluorobenzyl)amino]ethanol:

62.19 g (0.828 mol) of 2-(N-methylamino)ethanol, 36 ml of water and 21.73 g (0.258 mol) of sodium bicarbonate are introduced into a round-bottomed flask equipped with a magnetic stirrer. The mixture is stirred vigorously and heated to 90°–95° C. 30 g of 4-fluorobenzyl chloride are added dropwise, and the mixture is then maintained for 2 hours at 90°–95° C. After the mixture is cooled to room temperature, 50 ml of water are added and the precipitated salts are filtered off. The filtrate is extracted with twice 200 ml of chloroform, and the chloroform layer is washed twice with 50 ml of water and then dried over anhydrous magnesium sulphate. The solvent is evaporated off under vacuum. 28.2 g (74.4%) of a clear oil are obtained. The product is pure enough to be used as it is in the following stage.

IR spectrum (KBr)

3,600–3,200 cm$^{-1}$ (OH)
1,620 cm$^{-1}$ (C=C, aromatic)
1,540 cm$^{-1}$ (aromatic)

(b) 2-[N-Methyl-N-(4-fluorobenzyl)amino]ethyl acetylacetate:

A mixture of 18.2 g (99 mmol) of 2-[N-methyl-N-(4-fluorobenzyl)amino]ethanol and 36 g of anhydrous sodium acetate is heated to 75°–85° C. in a round-bottomed flask equipped with a magnetic stirrer, a reflux condenser, a thermometer and dropping funnel. When the temperature is reached, 7.67 ml (100 mmol) of ketene dimer are added dropwise, while the temperature is maintained at between 75° and 85° C. When the addition is complete, the mixture is maintained with stirring at the same temperature for one hour. The excess ketene is then removed under vacuum. 6.45 g (100%) of a brown oil are obtained, and this is used as it is for the following stage.

IR spectrum (KBr)

1,750 cm$^{-1}$ (C=O, ester)
1,720 cm$^{-1}$ (C=O, keto group)

(c) 2-[N-Methyl-N-(4-fluorobenzyl)amino]ethyl 3-aminocrotonate:

13.5 g (50 mmol) of 2-[N-methyl-N-(4-fluorobenzyl)amino]ethyl acetylacetate are dissolved in 15 ml of dry methanol in a round-bottomed flask equipped with a gas inlet and a thermometer. The solution is cooled in an ice/water bath and a stream of dry ammonia is bubbled through the reaction mixture until the latter is saturated (generally achieved in 2 hours), the temperature being maintained below 25° C.. The solvent is evaporated off under vacuum until a black oil is obtained. 100 ml of petroleum ether (b.p. 60°/80° C.) are then added and the mixture is brought to boiling with vigorous stirring for 10 minutes. The solid residue is then removed. The solvent is evaporated off under vacuum, and 12.3 g (92% yield) of orange oil are obtained.

IR spectrum (KBr)
3,460 and 3,350 cm$^{-1}$ (NH$_2$)
1,660 cm$^{-1}$ (conjugated ester)
1,630 cm$^{-1}$ (C=C)

(d) 3-Methyl 5-{2-[N-methyl-N-(4-fluorobenzyl)amino]ethyl}1,4-dihydro-2,6-dimethyl-4-(2,3-methylenedioxyphenyl)-3,5-pyridinedicarboxylate hydrochloride 1.5 g (6 mmol) of methyl α-acetyl-β-(2,3-methylenedioxyphenyl)acrylate and 1.59 g (6 mmol) of 2-[N-methyl-N-(4-fluorobenzyl)amino]ethyl 3-aminocrotonate are dissolved in 7 ml of isopropanol. The mixture is left to stand for 24 hours at 37° C., in an oven. The solvent is evaporated off under vacuum and the residual oil is dissolved in 60 ml of chloroform. After the addition of 20 ml of 6N hydrochloric acid, the mixture is stirred for 10 minutes. The organic layer is separated off after settling has occurred, and dried over anhydrous magnesium sulphate, and the solvent is evaporated off under vacuum. The residue is dissolved in 10 ml of hot acetone and crystallizes on cooling. The solid is collected by filtration and washed with cold acetone. 1.3 g (40%) of the product are obtained in the form of a hydrochloride. M.p. 205°–206° C.

IR spectrum (KBr)
3,700–2,500 cm$^{-1}$ (several bands, amine hydrochloride and N—H of the dihydropyridine ring)
1,715 and 1,710 cm$^{-1}$ (C=O, ester)

Example VIII

3-Ethyl 5-{2-[N-methyl-N-(4-fluorobenzyl)amino]ethyl}1,4-dihydro-2,6-dimethyl-4-(2,3-methylenedioxyphenyl)-3,5-pyridinedicarboxylate.

1 g (3.8 mmol) of ethyl α-acetyl-β-(2,3-methylenedioxyphenyl)acrylate and 1.01 g (3.8 mmol) of 2-[N-methyl-N-(4-fluorobenzyl)amino]ethyl 3-aminocrotonate are dissolved in 6.5 ml of isopropanol. The solution is left to stand for 24 hours at 37° C. in an oven, and the solvent is then evaporated off under vacuum. The residual oil is dissolved in 55 ml of chloroform, and 17 ml of 6N hydrochloric acid are added. The mixture is stirred for 10 minutes. The organic layer is separated off after settling has occurred, and dried over anhydrous magnesium sulphate. After removal of the solvent under vacuum, the residual oil is dissolved in 8 ml of hot acetone and left to crystallize. 0.95 g (45.7% yield) of the product is obtained in the form of a hydrochloride. M.p. 221°–222° C.

IR spectrum (KBr)

3,600–2,300 cm$^{-1}$ (several bands, amine hydrochloride and N—H of the dihydropyridine ring)
1,705–1,695 cm$^{-1}$ (doublet, C=O, ester group)

EXAMPLE IX

3-Methyl 5-{2-[N-methyl-N-(2-thienylmethyl)amino]ethyl}1,4-dihydro-2,6-dimethyl-4-(2,3-methylenedioxyphenyl)-3,5-pyridinedicarboxylate.

(a) 2-[N-Methyl-N-(2-thienylmethyl)amino]ethanol:

This compound is prepared by the reaction of 2-chloromethylthiophene (Org. Syntheses col. vol. 3 page 197) and 2-(N-methylamino)ethanol, according to the process described in Example VIIa (78% yield).

The product is used as it is for the following stage, without purification.

IR spectrum (KBr)

3,600–3,200 cm$^{-1}$ (OH, hydrogen bond)

(b) 2-[N-Methyl-N-(2-thienylmethyl)amino]ethyl acetylacetate:

The product is prepared by the reaction of 2-[N-methyl-N-(2-thienylmethyl)amino]ethanol and ketene, according to the process described in Example VIIb (100% yield). The product is used for the following stage without any purification.

IR spectrum (KBr)

1,760 cm$^{-1}$ (C=O, ester)
1,730 cm$^{-1}$ (C=O, ketone group)

(c) 2-[N-Methyl-N-(2-thienylmethyl)amino]ethyl α-acetyl-β-(2,3-methylenedioxyphenyl)acrylate:

8.55 g (56.9 mmol) of 2,3-methylenedioxybenzaldehyde and 15 g (58.7 mmol) of 2-[N-methyl-N-(2-thienylmethyl)amino]ethyl acetylacetate are introduced into 35 ml of dry benzene in a round-bottomed flask equipped with a Dean and Stark separator containing dry benzene. The mixture is heated until dissolution is complete, and 0.2 ml of piperidine and 0.68 ml of glacial acetic acid are then added. The resulting solution is brought to reflux until no more water is removed (1.5 hours). The solvent is removed under vacuum and the residue is washed twice with 50 ml of 5% strength hydrochloric acid. The aqueous layer is removed and the residual oil is dissolved in 100 ml of chloroform. The chloroform solution is washed with twice 50 ml of 10% strength sodium hydroxide. The organic layer is separated off after settling has occurred, and dried over anhydrous magnesium sulphate, and the solvent is removed under reduced pressure. The oily residue is washed with a mixture of 30 ml of n-hexane and 3 ml of ether, to extract the unreacted aldehyde. The solvent is removed and the oil is dried under vacuum to extract the final traces. 11.5 g (52.6%) of an orange oil are obtained.

IR spectrum (KBr)

1,740 cm$^{-1}$ (C=O, ester)
1,710 cm$^{-1}$ (C=O, ketone group)
1,680 cm$^{-1}$ (C=C)

(d) 3-Methyl 5-{2-[N-methyl-N-(2-thienylmethyl-)amino]-ethyl}1,4-dihydro-2,6-dimethyl-4-(2,3-methylenedioxy-phenyl)-3,5-pyridinedicarboxylate hydrochloride:

3 g (8.07 mmol) of 2-[N-methyl-N-(2-thienylmethyl)-amino] ethyl α-acetyl-β-(2,3-methylenedioxyphenyl)acrylate and 0.929 g (8.07 mmol) of methyl 3-aminocrotonate are dissolved in 10 ml of isopropanol. The solution is left to stand for 24 hours at 37° C., and the solvent is then evaporated off under vacuum. The residual oil is dissolved in 100 ml of chloroform, and 4 times 30 ml of 6N hydrochloric acid are then added with stirring in the course of 10 minutes. The organic layer is collected and dried over anhydrous magnesium sulphate, and the solvent is removed under vacuum. The residual oil is taken up with 18 ml of hot acetone and left to crystallize. The crystals are separated off by filtration and washed with cold acetone. 2.2 g (52%) of the product are obtained in the form of a hydrochloride. M.p. 207°–209° C.

IR spectrum (KBr)

3,600–2,300 cm$^{-1}$ (several bands, amine hydrochloride and N—H of the dihydropyridine ring)
1,715–1,705 cm$^{-1}$ (doublet, C=O of the ester groups)

EXAMPLE X

3-Ethyl 5-{2-[N-methyl-N-(2-thienylmethyl)amino]ethyl}1,4-dihydro-2,6-dimethyl-4-(2,3-methylenedioxyphenyl)-3,5-pyridinedicarboxylate.

This compound is prepared from 2-[N-methyl-N-(2-thienylmethyl)amino]ethyl α-acetyl-β-(2,3-methylenedioxyphenyl)acrylate and ethyl 3-aminocrotonate, according to the process described in Example IXd (58.2% yield). The product is obtained in the form of a hydrochloride. M.p. 193°–195° C.

IR spectrum (KBr)

3,600–2,300 cm$^{-1}$ (several bands, amine hydrochloride and N—H of the dihydropyridine ring)
1,715–1,705 cm$^{-1}$ (C=O, ester)

EXAMPLE XI

3-Isopropyl 5-{2-[N-methyl-N-(4-fluorobenzyl)amino]ethyl}1,4-dihydro-2,6-dimethyl-4-(2,3-methylenedioxyphenyl)3,5-pyridinedicarboxylate.

(a) 2-[N-Methyl-N-(4-fluorobenzyl)amino]ethyl α-acetyl-β-(2,3-methylenedioxyphenyl)acrylate:

The product is prepared by the reaction of 2,3-methylenedioxybenzaldehyde with 2-[N-methyl-N-(4-fluorobenzyl)amino]ethyl acetylacetate, according to the process described in Example IXc (73.8% yield).

IR spectrum (KBr)

1,740 cm$^{-1}$ (C=O, ester)
1,720 cm$^{-1}$ (C=O, ketone group)
1,680 cm$^{-1}$ (C=C)

(b) 3-Isopropyl 5-{2-[N-methyl-N-(4-fluorobenzyl)amino]-ethyl}1,4-dihydro-2,6-dimethyl-4-(2,3-methylenedioxyphenyl)-3,5-pyridinedicarboxylate hydrochloride:

This compound is prepared from isopropyl 3-aminocrotonate and 2-[N-methyl-N-(4-fluorobenzyl)amino]ethyl α-acetyl-β-(2,3-methylenedioxyphenyl)acrylate, according to the process described in Example VIId. The product is obtained in the form of a hydrochloride, in a 36% yield. M.p. 194°–195° C.

IR spectrum (KBr)

3,600–2,400 cm$^{-1}$ (several bands, amine hydrochloride, and N—H of the dihydropyridine ring)
1,720 cm$^{-1}$ and 1,710 cm$^{-1}$ (C=O, ester groups)

EXAMPLE XII

3-Isopropyl 5-{2-[N-methyl-N-(2-thienylmethyl)amino]ethyl}1,4-dihydro-2,6-dimethyl-4-(2,3-methylenedioxyphenyl)-3,5-pyridinedicarboxylate.

The compound is prepared by the reaction of 2-[N-methyl-N-(2-thienylmethyl)amino]ethyl α-acetyl-β-(2,3-methylenedioxyphenyl)acrylate and isopropyl 3-aminocrotonate, according to the process described in Example VIId (48.3% yield). The product is obtained in the form of a hydrochloride. M.p. 180°–182° C.

IR spectrum (KBr)
3,600–2,300 cm$^{-1}$ (several bands, amine hydrochloride and N—H of the dihydropyridine ring) 1,715 cm$^{-1}$ and 1,705 cm$^{-1}$ (C=O, ester groups)

The examples which follow illustrate the manner in which the compounds of the invention may be incorporated into pharmaceutical compositions.

Example XIII
Tablets.
Each tablet contains:

| | |
|---|---|
| Active substance | 10 to 20.0 mg |
| Maize starch | 25.0 mg |
| Lactose | 190.0 mg |
| Gelatin | 1.5 mg |
| Talc | 12.0 mg |
| Magnesium stearate | 1.5 mg |

Example XIV
Sublingual tablets.
Each tablet contains:

| | |
|---|---|
| Active substance | 10 to 20.0 mg |
| Lactose | 85.0 mg |
| Agar | 5.0 mg |
| Talc | 5.0 mg |

Example XV
Soft capsules.
Each capsule contains:

| | |
|---|---|
| Active substance | 10 to 20.0 mg |
| Glycerin | 150.0 mg |
| Polyoxyethylene glycol 400 | 50.0 mg |
| Distilled water | 150.0 mg |
| Saccharin | 2.0 mg |

Pharmacology

The compounds of the present invention were tested for their calcium-inhibitory properties by standard methods applicable "in vitro". A few of the most active compounds "in vitro" were also tested "in vitro".

Methods (1) "in vitro" tests:
Inhibitory effects with respect to contractions of the rat aorta induced by 80 mM KCl.

The aorta of WISTAR rats (220–250 g), sacrificed by decapitation, are removed and placed in a 20-ml organ bath at a temperature of 34° C., containing a KREBS solution composed as follows (in mmol per liter): NaCl, 137; KCl, 2.7; MgCl$_2$.6H$_2$O, 1.04; CaCl$_2$.2H$_2$O, 0.8; Na$_2$HPO$_4$.H$_2$O, 0.42; NaHCO$_3$, 11.9; glucose, 5. This solution is oxygenated with a mixture of 95% of O$_2$ and 5% of CO$_2$ (Furchgott and Bhadakron, 1956).

After a 45-minute stabilization period under a tension of 2 g, the maximal contractions of the artery are induced by adding KCl to the bath until a final concentration of 80 mmol/liter is attained. After the contractions have stabilized, the compounds of the invention, or OXODIPINE as control substance, are added, leaving a period of at least 10 minutes for stabilizing the relaxation.

The compounds of the present invention are dissolved in ethanol to give concentrated solutions containing approximately 1 mg/ml, from which the dilutions used above, from 10$^{-13}$ to 10$^{-7}$M, are obtained by adding saline solution. The 50% inhibitory concentrations (IC$_{50}$) are determined by analysis of the straight regression line.

(2) "In vivo" tests:

(2)1- antihypertensive activity:

A few compounds according to the invention were tested for their antihypertensive activity on conscious renal hypertensive rats. The systolic blood pressure was measured on the tail of unanaesthetized rats by means of an inflatable sleeve and an L.H.5 000 digital pressure gauge (Letica Instruments, Barcelona, Spain). The measurements were carried out before the i.p. administration of the test substance, and then 30 minutes, 1, 2, 4 and 5 hours after administration. The animals were maintained in preheated plastic cylinders during the measurements. Rats having a blood pressure of less than 160 mmHg were eliminated from the experiment.

Each compound was administered in 5% strength suspension (CMC) by i.p. injection.

(2)2- LD$_{50}$ (50% lethal dose):

The acute toxicity of a few compounds of the invention was determined in mice according to the method of LICHFIELD and WILCOXON. Groups of 5 mice weighing 20–25 g were treated with increasing i.p. doses of the test compounds. The mortality was recorded in the 7 days following the treatment, and the LD$_{50}$ calculated on this basis.

(2)3- Vascular activity in dogs:

Substances exhibiting a particular tropism for the coronary vessels may be turned to good account in the treatment of cardiac ischaemia, inasmuch as these substances increase the blood oxygen supply to the myocardium by a preferential coronary vasodilatory effect, and at the same time reduce the myocardial oxygen requirement. The beneficial effects on the oxygen supply/consumption balance may be accompanied by a modification of the blood distribution within the wall, which will be better irrigated, and by an increase in the blood flow in the collateral vessels during an acute occlusion of the coronary artery.

The effects of the compound of Example 11, at doses of 10 and less than 10 μg/kg i.v., were explored in anaesthetized dogs in order to determine:

- the regional (endocardium, epicardium) myocardial blood flows in the ischaemic and non-ischaemic zones,
- the ratio between the endo- and epicardial flows and the ratio of the flows in the ischaemic/nonischaemic zone,
- the regional blood flows in other areas (spleen, pancreas, kidney, liver, stomach, intestines, muscle, skin) in order to define the selectivity of action of the compound.

The studies were carried out on 6 adult dogs, according to the technique of BERDEAUX and GIUDICELLI (J. Pharmacol. 1985 - 16 - 59 ÷ 74 and J. Pharmacol. Exp. Ther. 1982, 221, 740–747). In addition, the haemodynamic parameters (heart rate, arterial blood pressure, left ventricular pressure, cardiac flow, total peripheral resistance, systolic ejection volume, cardiac work, contractility index) were monitored at regular times, before and after 3 successive short periods (12 minutes) of total occlusion of the coronary artery, the injection of radioactive microspheres enabling the regional flows to be evaluated. After the first period of ischaemia, the parameters were allowed to return to normal before the test compound was injected, the second occlusion was then performed and this procedure was repeated, the reversibility of the parameters being complete approximately 45 minutes after each occlusion.

The test compound was administered in aqueous-alcoholic solution (0.1 mg/ml) on the basis of 0.1 ml/kg i.v.

Results

The compounds according to the invention show a very high activity "in vitro" against KCl-induced contractions in rat aorta.

The following values were obtained ($IC_{50}$):
Example 1: $IC_{50} = 1.92 + 0.91 \times 10^{-6}M$
Example 2: $IC_{50} = 5.58 + 1.20 \times 10^{-7}M$
Example 4: $IC_{50} = 8.11 + 1.44 \times 10^{-8}M$
Example 5: $IC_{50} = 2.45 + 1.56 \times 10^{-7}M$
Example 6: $IC_{50} = 9.00 + 3.70 \times 10^{-9}M$
Example 3: $IC_{50} = 5.28 + 1.08 \times 10^{-8}M$
Example 7: $IC_{50} = 2.75 + 1.00 \times 10^{-9}M$
Example 8: $IC_{50} = 4.00 + 0.70 \times 10^{-11}M$
Example 9: $IC_{50} = 1.30 + 0.57 \times 10^{-8}M$
Example 10: $IC_{50} = 9.04 + 2.18 \times 10^{-10}M$
Example 11: $IC_{50} = 4.10 \times 1.52 \pm 10^{-11}M$
Example 12: $IC_{50} = 2.25 \pm 1.33 \times 10^{8}M$
OXOPIDINE $IC_{50} = 3.10 \pm 2.1 \times 10^{-9}M$ In vivo, the compounds of Examples 8 and 11 showed a marked antihypertensive activity on renal hypertensive rats, a dose of 1 mg/kg decreasing by 23 and 33%, respectively, the original high pressure. The effects of the compound of Example 11 were observed for more than 6 hours, while those of the compound of Example 8 were more temporary.

The intraperitoneal $LD_{50}$ of these two compounds in mice is:
Example 8 ... $LD_{50} = 70-80$ mg/kg
Example 11 ... $LD_{50} = 30-40$ mg/kg
OXODIPINE ... $LD_{50} = 30-40$ mg/kg The tests performed in dogs showed that the compound of Example 11 possesses potent coronary vasodilatory properties:

In the non-ischaemic zones, it decreases the coronary vascular resistance ($-38\%$ $p<0.05$) and increases the epicardial flow ($+62\%$ $p<0.001$) and the endocardial flow ($+26\%$ $p<0.05$), the endo/epi ratio being reduced by $-22\%$ ($p<0.001$). The transmural flow is increased by 42%. In parallel, the total peripheral resistance is reduced by 20%, showing the selectivity of action of the compound on the coronary vessels (where the resistance is decreased by 38%). The arterial blood pressure and heart rate are decreased ($-13\%$ and $-9\%$, respectively), while the contractility remains unchanged, and the cardiac flow is increased ($+9\%$) as well as the systolic ejection volume ($+18\%$). The concomitant decrease in the cardiac flow and the after-load (total peripheral resistance) reduces the myocardial oxygen consumption.

In the ischaemic zones, the epicardial flow is increased by 20% and more, the endocardial flow is maintained; the endo/epi ratio being reduced by $-21\%$ ($p<0.05$). These modifications are linked to the increased flow in the vessels collateral to the ischaemic zones.

In the other tissues and organs, the resistances are unmodified or slightly decreased under the action of the compound of Example 11, thereby showing the selectivity of effect at the level of the coronary vessels.

NIFEDIPINE, at 3 mg/kg/min and above, behaves differently, since it decreases the myocardial regional flows whereas the perfusion pressure is strongly reduced, and the heart rate increased (SELWYN et al. Circ. Res. 1979, 44, 16–22).

In conclusion, the use of the compounds of the invention in the treatment of angina pectoris represents a genuine advance.

We claim:

1. 1,4-Dihydropyridines of the following formula (III):

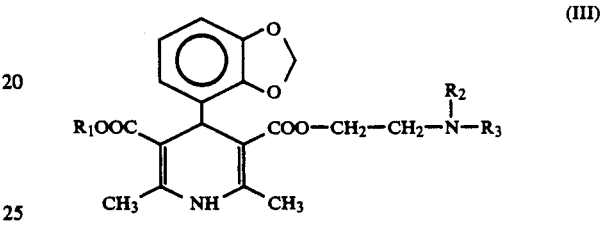

in which:
$R_1$ is a linear or branched $C_1$-$C_4$ alkyl group,
$R_2$ is formyl or a $C_1$-$C_2$ alkyl group,
$R_3$ is a 2-, 3- or 4- picolyl, 2-thienylmethyl, or 4-fluorobenzyl group,
or a pharmaceutically acceptable salt thereof with an inorganic or organic acid.

2. The compound of claim 1, which is 3-methyl 5-{2-(N-formyl-N-methyl(amino)ethyl} 1,4-dihydro-2,6-dimethyl-4-(2, 3-methylenedioxyphenyl)-3,5-pyridinedicarboxylate.

3. The compound which is 3-methyl 5-{2-(N-formyl-N-benzyl(amino)ethyl} 1,4-dihydro-2,6-dimethyl-4-(2,3-methylenedioxyphenyl)-3,5-pyridinedicarboxylate.

4. A compound of claim 1, which is 3-methyl 5-{2[N-methyl-N(2-picolyl)amino]ethyl} 1,4-dihydro-2,6-dimethyl-4-(2,3-methylenedioxyphenyl)-3,5-pyridinedicarboxylate.

5. A compound of claim 1, which is 3-methyl 5-{2-[N-methyl-N-(4-picolyl)amino]ethyl} 1,4-dihydro-2,6-dimethyl-4-(2,3-methylenedioxyphenyl)-3,5-pyridinedicarboxylate.

6. A compound of claim 1, which is 3-methyl 5-{(2-[N-methyl-N-(3-picolyl)amino]ethyl} 1,4-dihydro-2,6-dimethyl-4-(2,3-methylenedioxyphenyl)-3,5-pyridinedicarboxylate.

7. A compound of claim 1, which is 3-methyl 5-{2-[N-methyl-N-(4-fluorobenzyl)amino]ethyl} 1,4-dihydro-2,6-dimethyl-4-(2,3-methylenedioxyphenyl)-3,5-pyridinedicarboxylate.

8. A compound of claim 1, which is 3-ethyl 5-{2-[N-methyl-N-(4-fluorobenzyl)amino]ethyl} 1,4-dihydro-2,6-dimethyl-4-(2,3-methylenedioxyphenyl)-3,5-pyridinedicarboxylate.

9. A compound of claim 1, which is 3-methyl 5-{2-[N-methyl-N-(2-thienylmethyl)amino]ethyl} 1,4-dihydro-2,6-dimethyl-4-(2-,3-methylenedioxyphenyl)-3,5-pyridinedicarboxylate.

10. A compound of claim 1, which is 3-ethyl 5-{2-[N-methyl-N-(2-thienylmethyl)amino]ethyl} 1,4-dihydro-2,6-dimethyl-4-(2,which is 3-methylenedioxyphenyl)-3,5-pyridinedicarboxylate.

11. A compound of claim 1, which is 3-isopropyl 5-{2-[N-methyl-N-(4-fluorobenzyl)amino]ethyl} 1,4-dihydro-2,6-dimethyl-4-(2,3-methylenedioxyphenyl)-3,5-pyridinecarboxylate.

12. A compound of claim 1, which is 3-isopropyl 5-{2-[N-methyl-N-(2-thienylmethyl)amino]ethyl} 1,4-dihydro-2,6-dimethyl-4-(2,3-methylenedioxyphenyl)-3,5-pyridinedicarboxylate.

13. A method of treatment of hypertension, cardiac ischaemia or angina pectoris by administering to a human host a therapeutically effective amount of a compound of claims 1, 2, 3, 4, 5, 6, 7, 8, 9, 10, 11 or 12.

14. A pharmaceutical composition, the composition comprising a compound of claims 1, 2, 3, 4, 5, 6, 7, 8, 9, 10, 11 or 12 in an amount effective in the treatment of hypertension, cardiac ischaemia or angina pectoris in combination with a pharmaceutically acceptable vehicle.

15. The pharmaceutical composition of claim 14 wherein the effective amount comprises a unit dosage of about 1–50 mg of said compound.

* * * * *

UNITED STATES PATENT AND TRADEMARK OFFICE
CERTIFICATE OF CORRECTION

PATENT NO. : 4,952,592
DATED : August 28, 1990
INVENTOR(S) : Torija et al.

It is certified that error appears in the above—identified patent and that said Letters Patent is hereby corrected as shown below:

Column 9, line 65, substitute "6.45 g" with --26.45 g--.

Column 10, line 24, after "(4-fluorobenzyl", remove [-], keeping ")" immediately after fluorbenzyl.

Column 11, line 62, after "2-thienylmethyl", remove [-], keeping ")" immediately after thienylmethyl.

Column 12, line 54, after "(4-fluorobenzyl", remove [-], keeping ")" immediately after fluorobenzyl.

Column 13, line 49, change "in vitro" to --in vivo--.

Column 13, line 55, change "aorta" to --aortas--.

Column 15, line 29, change "4.10X1.52$^{\pm}$ to --4.10+1.52X--.

Signed and Sealed this

Seventh Day of April, 1992

Attest:

HARRY F. MANBECK, JR.

Attesting Officer      Commissioner of Patents and Trademarks